US006281678B1

(12) United States Patent
Auville

(10) Patent No.: US 6,281,678 B1
(45) Date of Patent: Aug. 28, 2001

(54) TRI-TIP PROBE

(76) Inventor: Gene R Auville, 441 Taylor St., Ashland, OR (US) 97520

( * ) Notice: Subject to any disclaimer, the term of this patent is extended or adjusted under 35 U.S.C. 154(b) by 0 days.

(21) Appl. No.: 09/515,932

(22) Filed: Feb. 29, 2000

(51) Int. Cl.[7] ............................. G01N 27/90; G01R 33/12
(52) U.S. Cl. ........................................ 324/220; 324/227
(58) Field of Search ........................... 324/219, 220, 324/221, 227, 228, 234, 236, 237, 238, 239, 240, 242, 243, 262

(56) References Cited

U.S. PATENT DOCUMENTS

| | | |
|---|---|---|
| 4,855,677 | 8/1989 | Clark, Jr. et al. . |
| 5,049,817 | 9/1991 | Cecco et al. . |
| 5,068,608 | 11/1991 | Clark, Jr. . |
| 5,237,270 | 8/1993 | Cecco et al. . |
| 5,270,647 | 12/1993 | Beissner et al. . |

*Primary Examiner*—Walter Snow
(74) *Attorney, Agent, or Firm*—Michael I. Kroll

(57) ABSTRACT

The present invention discloses 10 discloses an eddy current probe assembly having unique types and arrangements of coils 14, 16, 18 therein. This type and arrangement of coils allows for a more accurate determination of tube 20 anomalies. A first pair of coils 14 are provided which comprise a pair of coils 14A, 14B oriented 45 degrees apart wherein each pair of coils comprises an additional pair of coils 14G, 14H which are oriented 90 degrees apart. A second pair of coils 16 are provided which are about 0.060 inches apart. A third pair of coils 18 are provided having a larger coil 18A and a smaller coil 18B. An extension wand 22 with cable connectors 26 are provided for connection to suitable probe actuation and control means.

12 Claims, 7 Drawing Sheets

TRI-TIP PROBE

BACKGROUND OF THE INVENTION

1. Field of the Invention

The present invention relates generally to testing equipment and, more specifically, to testing equipment for eddy current tube analysis. The present invention, a triple-action heat exchanger tube probe, is an electromagnetic probing device attached to a long flexible extension means which is, in turn, connected by electrical wiring running therethrough, to an analyzing device. The purpose of this type of device is to provide a means of probing and detecting defects within non-ferrous heat exchanger tubing material. This can be accomplished by providing an electromagnetic transmitting coil within the probe that can induce eddy currents through some distance within the tubing material in order to produce a corresponding magnetic field therein that will indirectly cause an induced output current to be produced within a receiving coil in the probe that may then be transmitted to analyzing equipment. Thereupon the input/output currents are compared with calibrated standards and algorithms used by specialized diagnostic software programs running on test equipment for a determination of the defect condition of the material under test. Because of limitations in computer technology test probes have been limited to using one the of electromagnetic coil pair per test.

Recent advances in computer technology, however, have lead to the development of test equipment with multiple input/output signal generating and processing capability allowing for the support of multiple-coil pair use in test probes. This breakthrough technology now yields more information per test than was possible with previous testing techniques. This is accomplished by focusing on the advantages of each coil pair and ignoring the disadvantages. The results of this technique yield great benefits. The preferred embodiment of the present invention, the Tri-Tip Probe, is a prime example of the new technology that provides a unique assembly of 3 distinct coil pair types.

The first coil pair in the assembly is known as the AC3 coil pair. They specialize in electronically erasing all gradual geometry changes and detect large defects within these areas. It is positioned first in the probe assembly in order to be effective in testing through the end of the tube.

The middle coil pair, known as the Differential coil pair, excel at detecting small defects and making accurate depth determinations on both the inside and outside of the tube but cannot be used to determine overall wear patterns.

The last coil pair in the Tri-Tip Probe assembly is known as the x-axis coil pair. X-axis coil configuration is excellent at detecting overall wear patterns on both sides of the tube because it faithfully follows the tube geometry. The composite radiation pattern results in a large lobe of energy that can be rotated to further troubleshoot located defects.

Each of these coil pairs adds data missed by the others and the composite effect removes all the disadvantages inherent in each pair separately. With its unique combination of coil pairs, The Tri-Tip Probe can provide more information from a single test then was previously possible from any other probe or series of individual tests.

2. Description of the Prior Art

There are other eddy current probing devices designed for eddy current tube analysis. Typical of these is U.S. Pat. No. 5,270,647 issued to Robert Beissner and Takashi Kikuta on Dec. 14, 1993.

Another patent was issued to Valentino S. Cecco et al. on Aug. 17, 1993 as U.S. Pat. No. 5,237,270. Yet another U.S. Pat. No. 4,855,677 was issued to William G. Clark et al. on Aug. 8, 1989 and still yet another was issued on Sep. 17, 1991 to Valentino S. Cecco et al. as U.S. Pat. No. 5,049,817.

Another patent was issued to William G. Clark on Nov. 26, 1991 as U.S. Pat. No. 5,068,608.

U.S. Pat. No. 5,270,647

Inventor: Robert Beissner & Takashi Kikuta

Issued: Dec. 14, 1993

A pipe electromagnetic field simulation apparatus used to simulate a current produced by flaw in a pipe when the flaw is subjected to the electromagnetic field of a transmitting coil. The apparatus includes a system for determining an electromagnetic field distribution of a represented pipe without a flaw, a system for determining an equivalent current source of a represented flaw in the represented pipe, and a system for determining the electromagnetic field distribution of a represented pipe with a flaw. The apparatus may also include a system for determining a signal received by a detector which indicates a flaw.

U.S. Pat. No. 5,237,270

Inventor: Valentino S. Cecco and Jon R. Carter

Issued: Aug. 17, 1993

Eddy current probes for ferromagnetic tubes of relatively small diameters are disclosed. A probe housing is made of non-ferromagnetic material and shaped to be introduced into a tube for inspection. The probe housing includes at least two eddy current measuring assemblies either of these assemblies includes magnetic field generators for producing a maximum magnetization at a predetermined area of the tube and a minimum magnetization at a diametrically opposite area of the tube. At least on eddy current measuring coil is associated with each magnetic field generator to measure the eddy current generated in the tube and which has a relatively high sensitivity to an anomaly at the maximum magnetization area. Further the current measuring assemblies are spaced apart axially with the housing and are rotated about its central axis by a predetermined angle so that each assembly differs in sensitivity to an anomaly depending upon their location within the housing.

U.S. Pat. No. 4,855,677

Inventor: William G. Clark, Jr. and Michael J. Metala

Issued: Aug. 8, 1989

An improved eddy current probe system and method for simultaneously detecting different types of flaws at different depths within a metallic wall, such as a section of Inconel tubing, is disclosed herein. The system comprises a current generator for generating alternating currents of substantially different frequencies, a probe head including first, second and third concentrically arranged coils in separate communication with a the current generator, shielding material disposed between the coils for preventing cross talk between the coil and the pulsating magnetic field of the coils adjacent to it, and a detector circuit which may include an inductive bridge for providing an electrical output representative of the impedance changes in the respective coils. In operation, each of the coils conduct currents having substantially different frequencies, the highest frequency being conducted by the smallest-diametered coil and the lowest frequency being conducted by the largest-diametered coil. The different levels of magnetic field penetration provided by the coils as it is helically moved around the inside surface of a section on Inconel tubing not only allows the probe system to detect diverse kinds of flaws such as cracks, pits, or regions of thinning, but also flaws located at different depths throughout the tube wall. In the method of the invention, a computer is used to adjust the frequencies of the alternating currents conducted through the coils during the scanning operation in order to maximize the impedance changes in each coil, thereby maximizing the resolution of the probe system.

U.S. Pat. No. 5,049,817

Inventor: Valentino S. Cecco and F. Leonard Sharp

Issued: Sep. 17, 1991

Eddy current probes for detecting internal defects in a ferromagnetic tube are disclosed. The probe uses a plurality of eddy current measuring means, each being operated at a different operating point on the impedance diagram. By operating more that one such eddy current measuring means simultaneously, noises by, for example, permeability variation of a ferromagnetic material and internal magnetic deposit, can be made less influential.

U.S. Pat. No. 5,068,608

Inventor: William G. Clark, Jr.

Issued: Nov. 26, 1991

Both a system and a method for determining the length of a discontinuity such as a crack or other fault in the interior wall of a steam generator heat exchanger tube is disclosed herein. The apparatus generally comprises an elongated probe assembly which includes a plurality of eddy current coils mutually separated at known distances with respect to each other along the longitudinal axis of the probe, and an eddy current coil actuating device for separately and independently actuating each of the coils to provide an adjustable electromagnetic sensing field. In the method of the invention, the probe assembly is positioned adjacent a discontinuity and then each eddy current coil, separated by a known distance, is independently actuated and its reading recorded to determine which of the coils actually detects the discontinuity. The length of the discontinuity may then be generally inferred from the known distances that separate the eddy current coils that detect the extremities of the crack or other discontinuity. A more specific sizing of the length of the crack is then obtained by actuating the eddy current coils that are located just outside the extremity-detecting coils at progressively lower frequencies until field of the outside coils finally couples with the extremities of the crack.

While these eddy current probes may be suitable for the purposes for which they were designed, they would not be as suitable for the purposes of the present invention, as hereinafter described.

SUMMARY OF THE PRESENT INVENTION

The present invention discloses an eddy current probe assembly having unique types and arrangements of coils therein. This type and arrangement of coils allows for a more accurate determination of tube anomalies. A first pair of coils are provided which consist of a pair of coils oriented 45 degrees apart wherein each pair of coils comprises an additional pair of coil windings which are oriented 90 degrees apart. A second pair of coils are provided which are about 0.060 inches apart. A third pair of coils are provided having a larger coil and a smaller coil. An extension wand with cable connectors are provided for connection to suitable probe actuation and control means.

A primary object of the present invention is to provide a means of probing, detecting defects and analyzing all defects in non-ferrous heat exchanger tubing.

Another object of the present invention is to improve the accuracy of probing, detecting defects and analyzing all defects in non-ferrous heat exchanger tubing.

Still another object of the present invention is to help eliminate the ambiguity of some defects in non-ferrous heat exchanger tubing.

Another object of the present invention is amplify the small defects on the inside of non-ferrous tubing used in heat exchangers without increasing the noise.

Still another object of the present invention is amplify the small defects on the outside of non-ferrous tubing used in heat exchangers without increasing the noise.

Yet another object of the present invention is to reduce the effects of changes in permeability due to blending of metals in non-ferrous tubing used in heat exchangers.

Yet still another object of the present invention is to reduce the effects of changes in conductivity due to blending of metals in non-ferrous tubing used in heat exchangers.

Still yet another object of the present invention is to reduce or eliminate the effects of geometry changes located in non-ferrous tubing used in heat exchangers.

Yet another object of the present invention is to reduce the errors of depth of wall penetration caused by sophisticated fins on both the inside and outside of non-ferrous tubing used in heat exchangers.

Still yet another object of the present invention is to improve the linear presentation of all defects located in the non-ferrous tubing found in heat exchangers. The equipment and software will have improved data to apply to the analysis curve resulting in test repeatability.

Another object of the present invention is to stay abreast of the more sophisticated non-ferrous tubing now being introduced in the heat exchange industry.

Yet another object of the present invention is to enable a faster and more thorough examination of the non-ferrous tubing used in heat exchangers.

Still another object of the present invention is to provide a test reliable enough to allow trend analysis over time on the non-ferrous tubing in heat exchangers.

Yet still another object of the present invention is to test 100% of each non-ferrous tube used in heat exchangers from crown sheet to crown sheet which includes all distorted fin and land areas.

Additional objects of the present invention will appear as the description proceeds.

The present invention overcomes the shortcomings of the prior art by providing a triple-action heat exchanger tube probe, an electromagnetic probing device attached to a long flexible extension means which is, in turn, connected by electrical wiring running therethrough, to an analyzing device. Because of limitations in computer and testing technology previous types of probes have been limited to using one type of electromagnetic coil pair per test.

Recent advances in computer technology, however, have lead to the development of test equipment with multiple input/output signal generating and processing capability allowing for the support of multiple-coil pair use in test probes. This breakthrough technology now yields more information per test than was possible with previous testing techniques. The preferred embodiment of the present invention, the Tri-Tip Probe, is a prime example of the new technology that provides a unique assembly of 3 distinct coil pair types.

The first coil pair in the assembly is known as the AC3 coil pair. Each coil in this pair is actually a set of two coils wound from a single wire about a rectangular plastic core, each offset 90° from the other with the elongated sides oriented axially with the probe tube housing. The plastic core of the coil is actually a cylinder from which equal rectangular portions have been removed radially as well as equally from both ends to provide uniform channels for the coil windings. The remaining portions of the cylinder surfaces serve to centralize the finished coil in the tube cavity. The second duplicate set of coils is located axially adjacent to the first set with its coils angularly offset 45° from those of the first. AC3 coil pairs excel at removing gradual geometry changes caused by tube manufacturing. This allows detection of circumferential cracks caused by machine operation. This set of coils is placed first in the probe housing so the final few inches of the tube can be tested since it involves this geometry change.

The middle coil pair is known as the Differential coil pair. Each coil is wound in opposite directions around a single plastic cylindrical core 0.060" apart. The coil windings are oriented circumferentially to the probe tube housing. The lines of flux are adding in this narrow space thereby causing amplification. Differential coil pairs excel at detecting small defects and making accurate depth determinations on defects that start on the inside or outside of the tubing.

The last coil pair in the Tri-Tip Probe assembly is known as the x-axis coil pair. One coil is axially coincident and perpendicular with respect to the probe tube axis while the other adjacently positioned coil is coaxial. X-axis coil pairs excel at detecting overall wear patterns because it faithfully follows the tube geometry. It provides very accurate depth readings (+0.002 inch) for O.D. metal missing at the supports(saddle damage). Since the composite signal created by the coil arrangement develops a large lobe of energy, it can be used to troubleshoot.

Each of these coil pair not only adds information missed by the others but, because of their composite effect, allows the test to be performed much faster with greater accuracy and less likelihood of missing serious flaws. The Tri-Tip Probe, in cooperation with appropriate test analysis equipment, can provide a wealth of information from a single test, the scope and magnitude of which has not been previously possible from any single test or series of tests.

The foregoing and other objects and advantages will appear from the description to follow. In the description reference is made to the accompanying drawings, which form a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawings, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWINGS

In order that the invention may be more fully understood, it will now be described, by way of example, with reference to the accompanying drawings in which.

LIST OF REFERENCE NUMERALS

Figure 1:
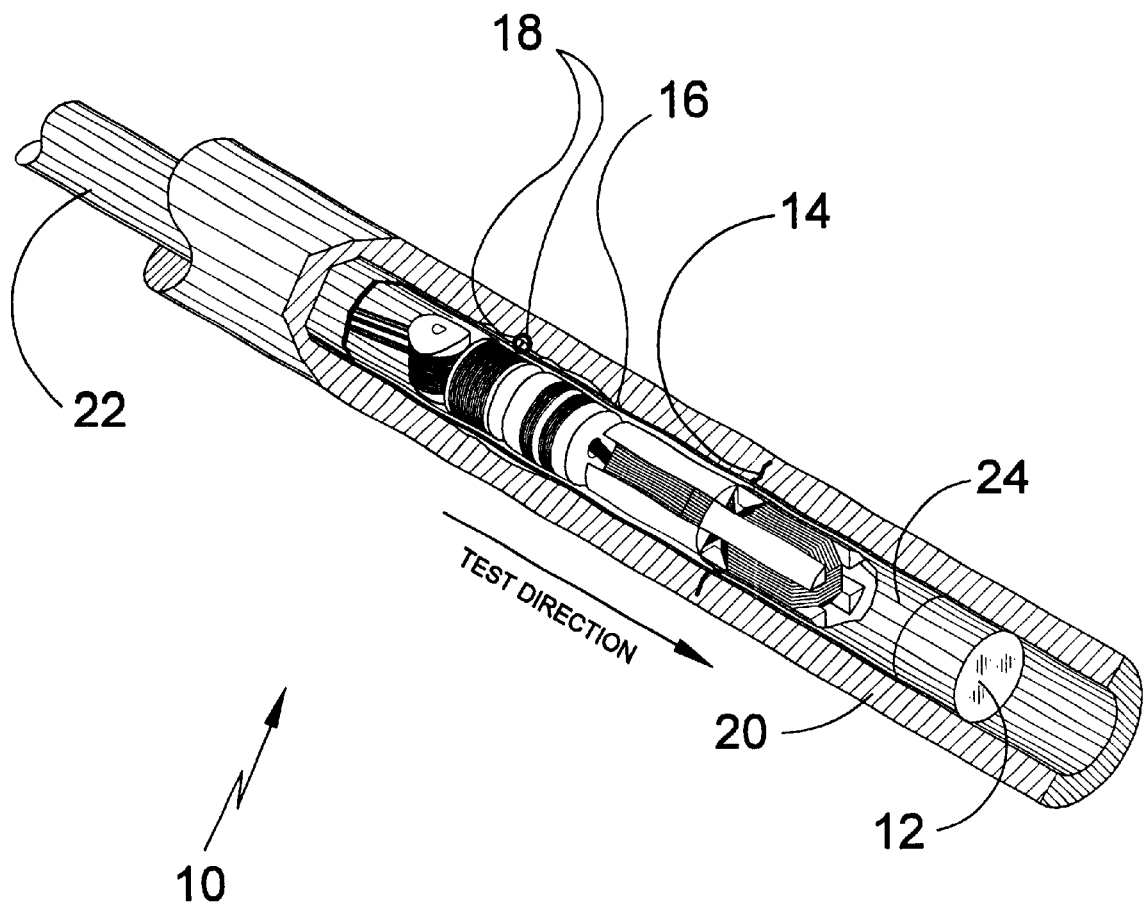
FIG. 1 is a perspective view of a broken out section of the present invention, the Tri-Tip Probe, showing the three coil pair assembly in use in detecting different types of anomalies in a broken out section of heat exchange tubing.

With regard to reference numerals used, the following numbering is used throughout the drawings.

10 present invention
12 probe tip
14 AC3 coil pair
14A first coil
14B second coil
14C coil wire
14D plastic core
14E core channel
14F coil windings
14G coil winding
14H coil winding
16 differential coil pair
16A first coil
16B second coil
16C coil wire
16D core
18 x-axis coil pair
18A larger coil
18B smaller coil
20 heat exchange tubing
22 extension wand
24 probe casing
26 cable connectors
28 end cap

DESCRIPTION OF THE PREFERRED EMBODIMENT(S)

In order that the invention may be more fully understood, it will now be described, by way of example, with reference to the accompanying drawings in which FIGS. 1 through 7 illustrate the present invention being a probe having three coil pairs.

Turning to FIG. 1, shown therein is a perspective view of a broken out section of the present invention 10, the tri-tip probe tip 12, showing the three coil pair assemblies 14, 16, 18 in use in detecting different types of anomalies in a broken out section of heat exchange tubing 20. Also shown is the extension wand 22 and probe casing 24 which is expected to be made of plastic or like non-metallic material as would be done by one skilled in the art.

Figure 2:
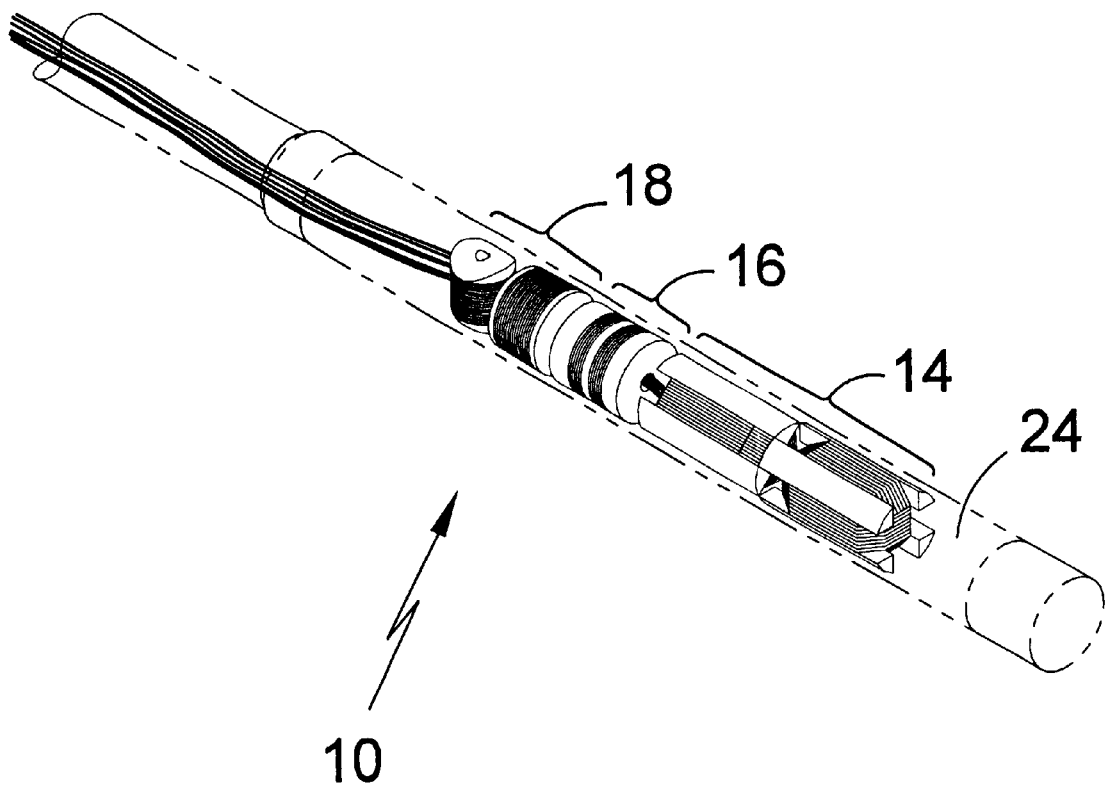
FIG. 2 is an interior perspective view of the triple action probe coil assembly consisting of three different types of coil pairs with the probe housing in phantom.

Turning to FIG. 2, shown therein is an interior perspective view of the present invention 10 with triple action probe coil assembly 14, 16, 18 consisting of three different types of coil pairs with the probe housing 24 in phantom. Shown are the AC3 coil pair 14 in the first position, the differential coil pair 16 in the second position, and the x-axis coil pair 18 in the third position taken from probe tip 12.

Figure 3:
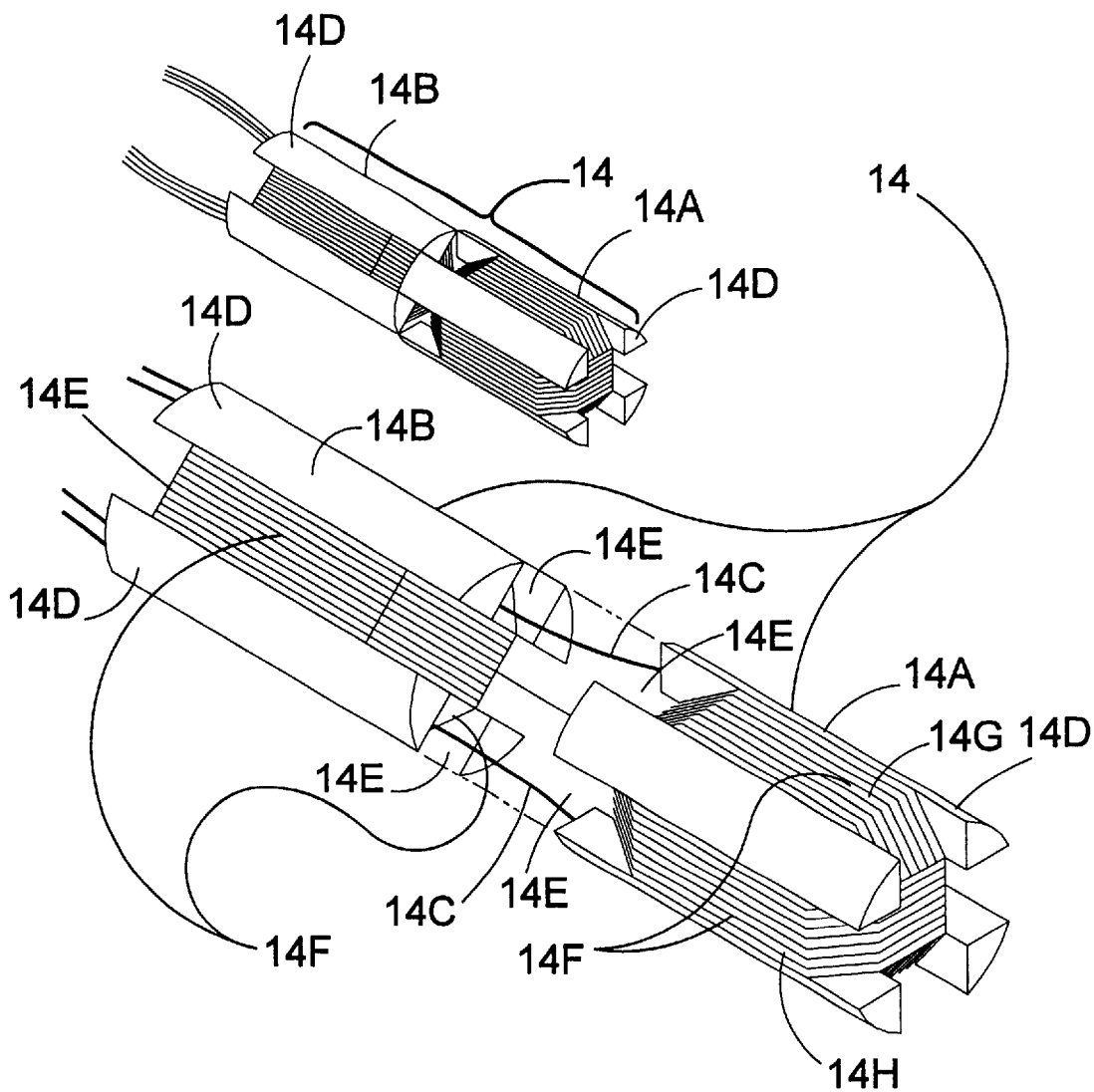
FIG. 3 is a perspective view of the AC3 coil pair. Each individual coil is actually a set of two coils wound about a single rectangular core, offset 90° from each other. The second adjacent coil set is identical except it is rotated 45° from the first.

Turning to FIG. 3, shown therein is a perspective view of the AC3 coil pair 14. Each coil 14A, 14B in this pair is actually a set of two coils wound from a single wire about a rectangular plastic core 14D, each offset 90° from the other with the elongated sides oriented axially with the probe tube housing. For example, coil 14A comprises two coils 14G and 14H wound from a single wire 14C. Likewise, coil 14B is similarly wound. The plastic core 14D of the coil is actually a cylinder from which equal rectangular portions have been removed radially as well as equally from both ends to provide uniform channels 14E for the coil windings 14F. The remaining portions of the cylinder surfaces serve to centralize the finished coil in the probe tube cavity. The second duplicate set of coils 14B is located axially adjacent to the first set 14A with its coils 14B angularly offset 45° from those of the first 14A. Coil pairs 14A, 14B are somewhat elliptically shaped having their centers or axis of rotation perpendicular to the longitudinal centerline or axis of the elongated probe assembly. AC3 coil pairs 14 excel at removing gradual geometry changes caused by tube manufacturing. This allows detection of circumferential cracks and pre-circumferential cracks caused by machine operation or otherwise. This set of coils 14 is placed first or to the front in the probe housing 24 so the final few inches of the tube 20 can be tested since it involves this geometry change.

Figure 4:
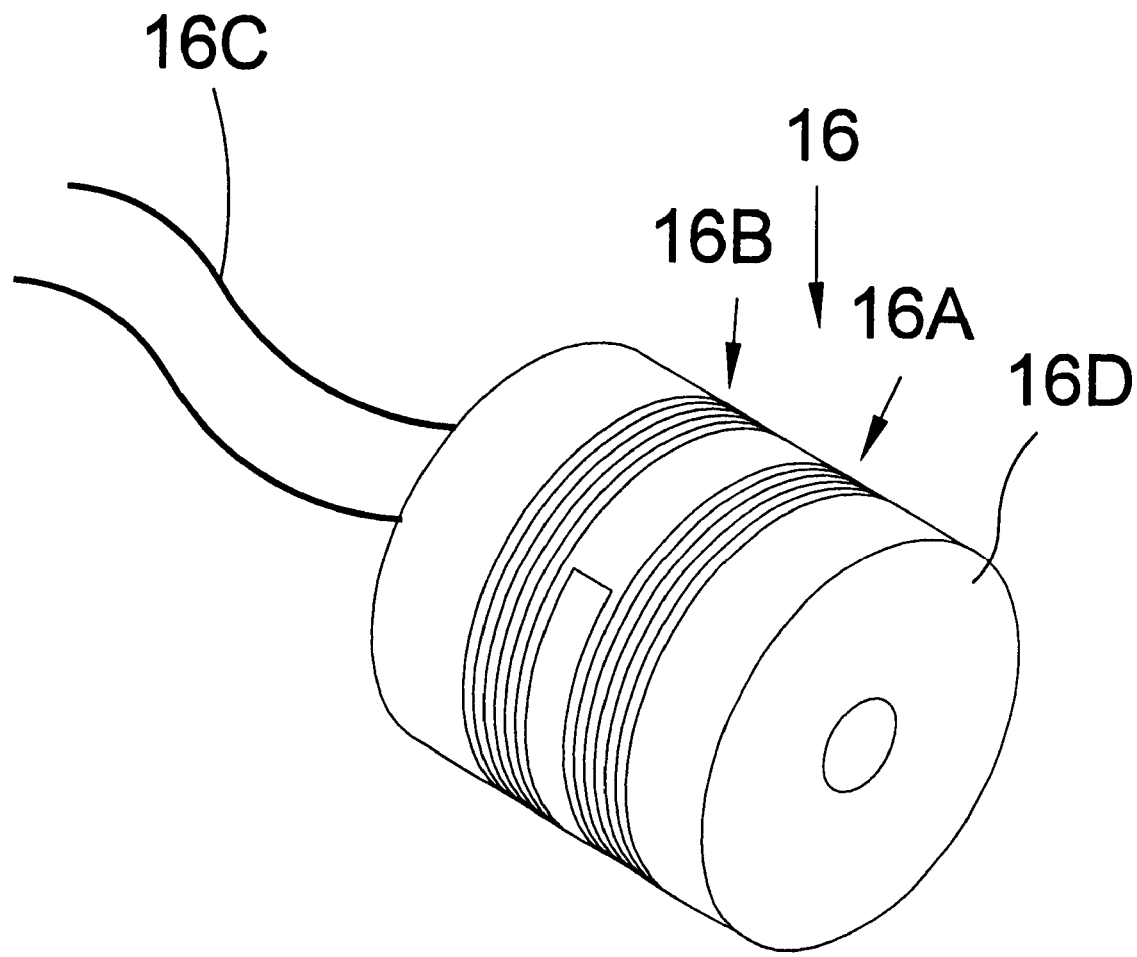
FIG. 4 is a perspective view of the differential coil pair. Each coil is wound in opposite directions a small distance apart around a single plastic cylindrical core. The coil windings are coaxial with respect to the probe tube housing.

Turning to FIG. 4, shown therein is a perspective view of the differential coil pair 16. The middle coil pair is known as the differential coil pair 16. Each coil 16A, 16B is wound in opposite directions around a single plastic cylindrical core 16D a small distance, i.e., about 0.060", apart. The coil windings are oriented coaxially or circumferentially to the probe tube housing so that their centers or axis of rotation are parallel to the longitudinal centerline or axis of the elongated probe assembly. Also shown is coil wire 16C. The lines of flux are adding in this narrow thereby causing amplification. Differential coil pairs 16 excel at detecting small defects on both sides of the tube and making accurate depth determinations throughout the tube wall on defects that start on the inside or outside of the tubing. Gradual wall thinning is not detected since the test area of the tube is only about 0.060 inch.

Figure 5:
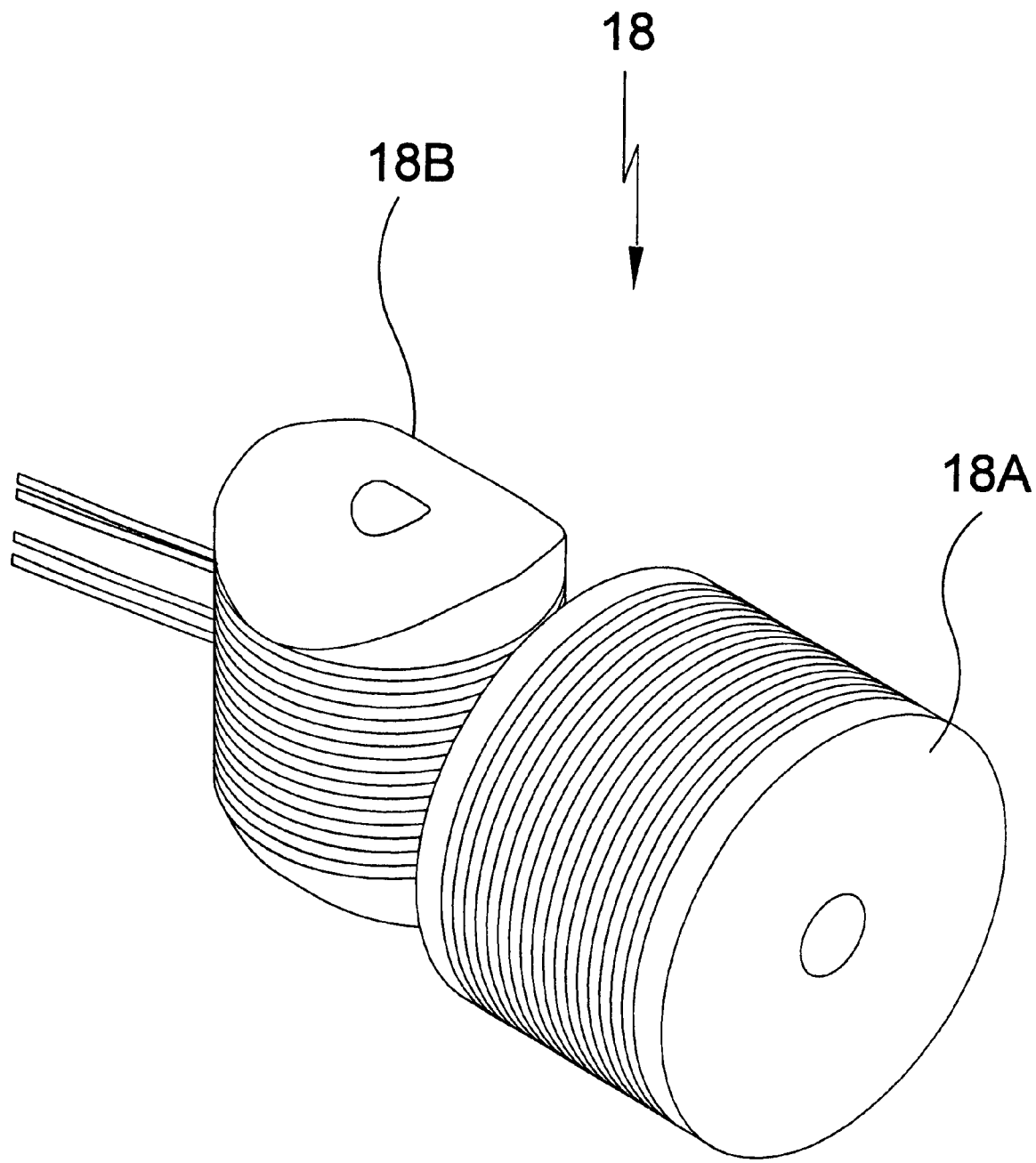
FIG. 5 is a perspective view of the x-axis coil pair. The smaller coil is manufactured and assembled so that it is centralized within the probe tube housing with its axis coincident and perpendicular to the probe tube axis while the larger adjacent one is coaxial with the housing.

Turning to FIG. 5, shown therein is a perspective view of the x-axis coil pair 18. The smaller coil 18B is manufactured and assembled so that it is centralized within the probe tube housing with its axis or center of rotation coincident and perpendicular to the probe tube axis while the larger adjacent coil 18A is coaxial with the housing having its center or axis of rotation parallel to the probe axis. This last coil pair in the tri-tip probe assembly is known as the x-axis coil pair 18. X-axis coil pairs excel at detecting overall wear patterns because it faithfully follows the tube geometry involving over 1 inch of tubing. It provides very accurate depth readings (+0.002 inch) for O.D. metal missing at the supports (saddle damage). Since the composite signal created by the coil arrangement develops a large lobe of energy, it can be used to troubleshoot freeze bulges and saddle damage. Each of these coil pairs not only adds information missed by the others but, because of their composite effect, allows the test to be performed much faster with greater accuracy and repeatability and less likelihood of missing serious flaws. The tri-tip-probe, in cooperation with appropriate test analysis equipment, can provide a wealth of information from a single test, the scope and magnitude of which has not been previously possible from any single test or series of tests. Also the present invention can detect the angular displacement of defects which has been heretofore impossible.

Figure 6:
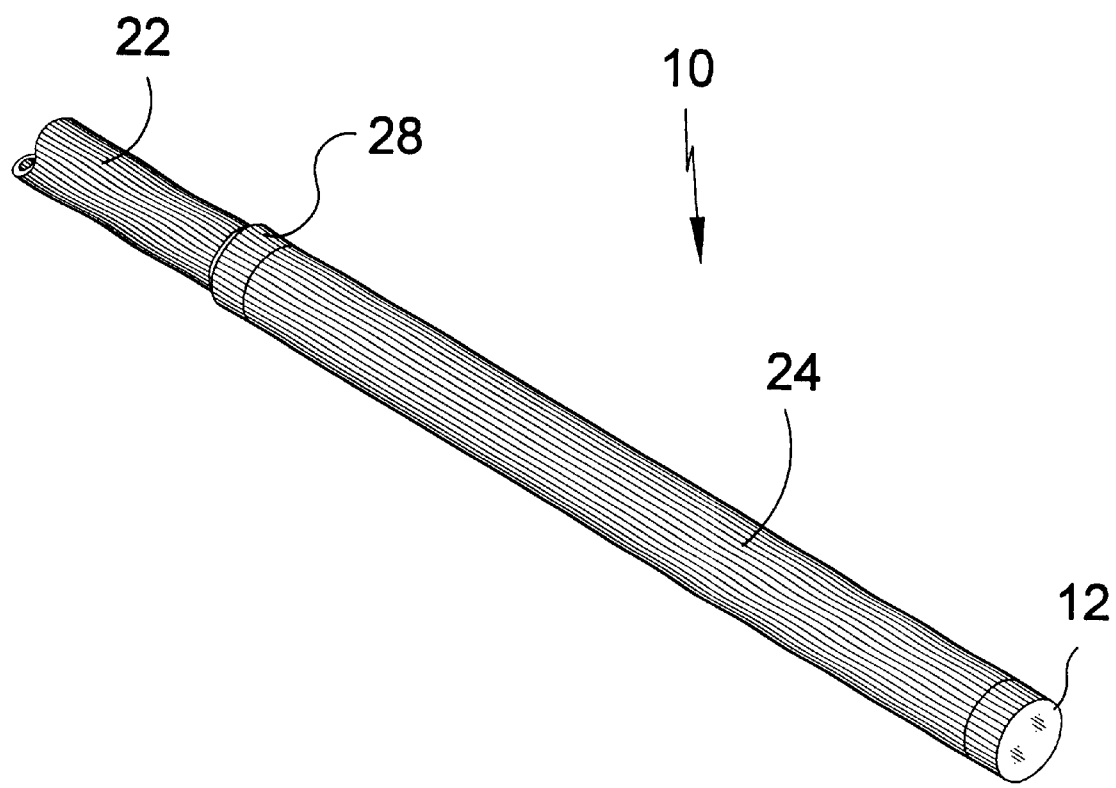
FIG. 6 is a perspective view of the triple action, heat exchanger tube probe

Turning to FIG. 6, shown therein is a perspective view of the triple action, heat exchanger tube probe 10 showing the probe tip 12, extension wand 22, probe casing 24 and enclosure end caps or coupling 28.

Figure 7:
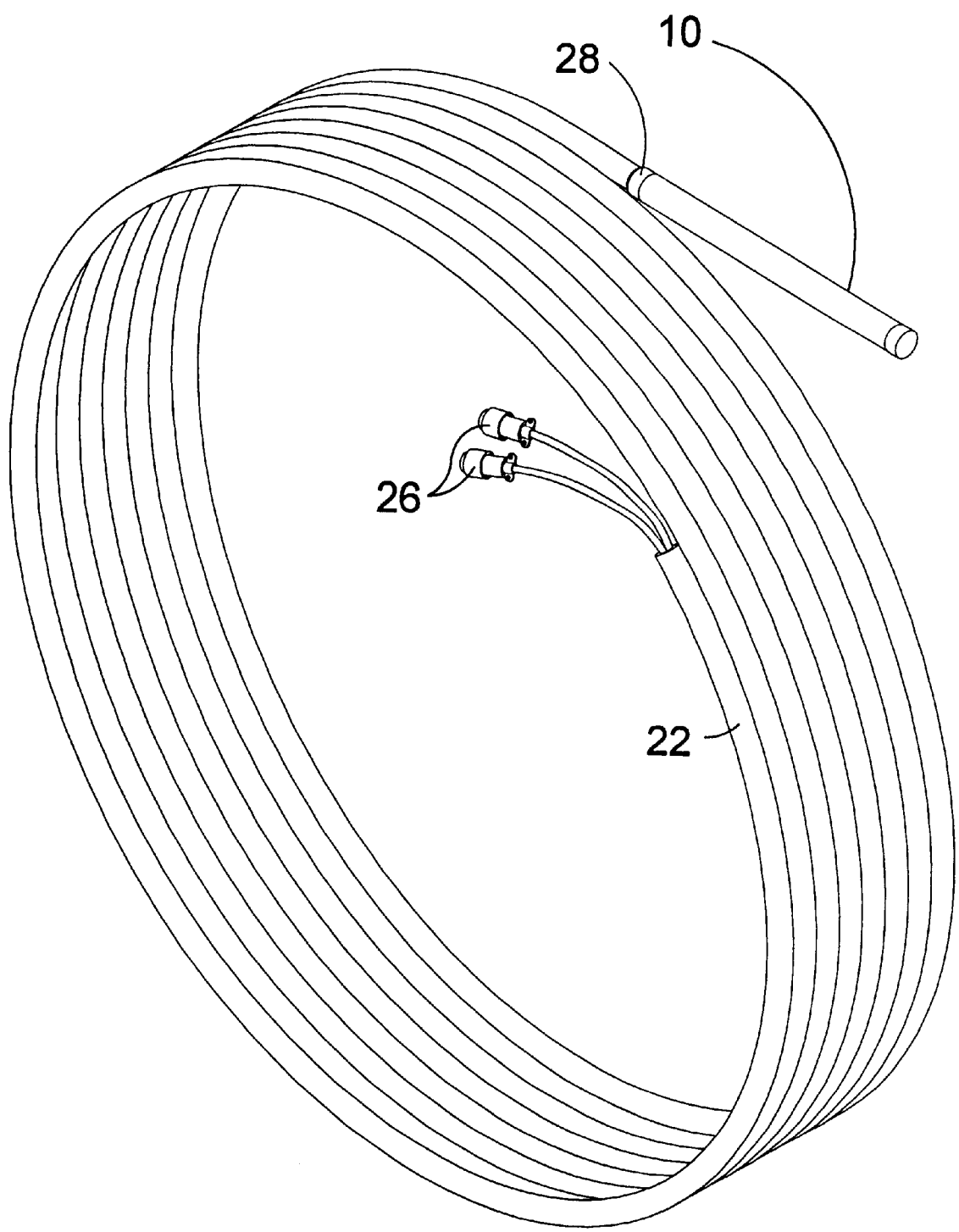
FIG. 7 is a perspective view of the triple action, heat exchanger tube probe with extension wand and two cable connectors.

Turning to FIG. 7, shown therein is a perspective view of the triple action, heat exchanger tube probe 10 with extension wand 22, two cable connectors 26 and end cap 28.

What is claimed to be new and desired to be protected by Letters Patent is set forth in the appended claims:

1. An apparatus for an eddy current probe for detecting anomalies in a tube, comprising:
   a) an elongated probe assembly having a central axis, said probe assembly having an array of coils disposed therein;
   b) a first pair of coils each having their axis of rotation perpendicular to said central axis of said elongated probe assembly;
   c) wherein each of said first pair of coils further comprises a first coil winding and a second coil winding, each having their axis of rotation perpendicular to said central axis of said elongated probe assembly;
   d) a second pair of coils each having their axis of rotation parallel to said central axis of said elongated probe assembly;
   e) a third pair of coils, wherein a first larger coil of said pair has its axis of rotation parallel to said central axis of said elongated probe assembly, and, a second smaller coil of said pair has its axis of rotation perpendicular to said central axis of said elongated probe assembly; and,
   f) a coil actuating means for energizing said first pair of coils, said second pair of coils, and third pair of coils whereby eddy currents are generated suitable for detecting anomalies in the tube.

2. The apparatus of claim 1, wherein said first pair of coils are oriented so that their windings are 45 degrees apart.

3. The apparatus of claim 1, wherein said first coil winding and said second coil winding of said first pair of coils are oriented so that their windings are 90 degrees apart.

4. The apparatus of claim 1, wherein said first coil winding and said second coil winding of said first pair of coils are substantially elliptically shaped.

5. The apparatus of claim 1, wherein said second pair of coils are about 0.060 inch apart.

6. The apparatus of claim 1, wherein said first pair of coils are positioned first in said elongated probe assembly, said second pair of coils are positioned second in said elongated probe assembly, and said third pair of coils are positioned third in said elongated probe assembly.

7. In an eddy current probe for detecting anomalies in a tube wherein the probe has an array of coils disposed therein and a means for actuating and controlling the array of coils so that eddy currents are generated thereby suitable for detecting anomalies in the tube, wherein the improvement comprising:
   a) an elongated probe assembly having a central axis;
   b) a first pair of coils each having their axis of rotation perpendicular to said central axis of said elongated probe assembly;
   c) wherein each of said first pair of coils further comprises a first coil winding and a second coil winding, each having their axis of rotation perpendicular to said central axis of said elongated probe assembly;
   d) a second pair of coils each having their axis of rotation parallel to said central axis of said elongated probe assembly; and,
   e) a third pair of coils, wherein a first larger coil of said pair has its axis of rotation parallel to said central axis of said elongated probe assembly, and, a second smaller coil of said pair has its axis of rotation perpendicular to said central axis of said elongated probe assembly.

8. The apparatus of claim 7, wherein said first pair of coils are oriented so that their windings are 45 degrees apart.

9. The apparatus of claim 7, wherein said first coil winding and said second coil winding of said first pair of coils are oriented so that their windings are 90 degrees apart.

10. The apparatus of claim 7, wherein said first coil winding and said second coil winding of said first pair of coils are substantially elliptically shaped.

11. The apparatus of claim 7, wherein said second pair of coils are about 0.060 inch apart.

12. The apparatus of claim 7, wherein said first pair of coils are positioned first in said elongated probe assembly, said second pair of coils are positioned second in said elongated probe assembly, and said third pair of coils are positioned third in said elongated probe assembly.

* * * * *